(12) United States Patent
Gnanaprakasam et al.

(10) Patent No.: US 8,293,894 B2
(45) Date of Patent: Oct. 23, 2012

(54) PROCESS FOR THE PREPARATION OF CARBAPENEM ANTIBIOTIC

(75) Inventors: Andrew Gnanaprakasam, Chennai (IN); Nagappan Arumugam, Chennai (IN); Palanisamy Senthilkumar Udayampalayam, Chennai (IN); Pandi Suresh Pandian, Chennai (IN); Venugopal Sivasankaran, Chennai (IN); Ganapathy Veeramani, Chennai (IN); Henry Syril Sudhan, Chennai (IN); Gollapalli Venkateswara Rao, Secundrabad (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 511 days.

(21) Appl. No.: 12/312,649

(22) PCT Filed: Nov. 20, 2007

(86) PCT No.: PCT/IB2007/003564
§ 371 (c)(1), (2), (4) Date: Jul. 1, 2009

(87) PCT Pub. No.: WO2008/062279
PCT Pub. Date: May 29, 2008

(65) Prior Publication Data
US 2009/0312539 A1 Dec. 17, 2009

(30) Foreign Application Priority Data

| Nov. 20, 2006 | (IN) | 2153/CHE/2006 |
| May 11, 2007 | (IN) | 1000/CHE/2007 |
| Jun. 29, 2007 | (IN) | 1395/CHE/2007 |

(51) Int. Cl.
*C07D 477/20* (2006.01)

(52) U.S. Cl. ...................................... 540/350
(58) Field of Classification Search .................. 540/350
See application file for complete search history.

(56) References Cited

U.S. PATENT DOCUMENTS

| 5,478,820 A | 12/1995 | Betts et al. |
| 5,856,321 A | 1/1999 | Betts et al. |
| 5,872,250 A * | 2/1999 | Williams et al. ............... 540/350 |
| 5,952,323 A | 9/1999 | Zimmerman et al. |
| 6,180,783 B1 * | 1/2001 | Williams et al. ............... 540/350 |
| 6,504,027 B1 | 1/2003 | Williams et al. |
| 7,022,841 B2 | 4/2006 | Cvetovich et al. |
| 7,145,002 B2 | 12/2006 | Brands et al. |
| 7,342,005 B2 * | 3/2008 | Betts et al. ............... 514/210.13 |
| RE40,794 E * | 6/2009 | Brands et al. ............... 540/350 |
| 2003/0144264 A1 | 7/2003 | Betts et al. |
| 2004/0235817 A1 * | 11/2004 | Brands et al. ............... 514/210.13 |
| 2011/0224426 A1 * | 9/2011 | Tewari et al. ............... 540/350 |
| 2011/0288289 A1 * | 11/2011 | Tseng et al. ............... 540/350 |
| 2011/0288290 A1 * | 11/2011 | Tseng et al. ............... 540/350 |

FOREIGN PATENT DOCUMENTS

| IN | 2007CH01890 A * | 3/2010 |
| WO | WO 02/057266 A1 | 7/2002 |
| WO | WO 2007029084 A2 * | 3/2007 |
| WO | WO 2010124531 A1 * | 11/2010 |

OTHER PUBLICATIONS

Williams, J. Org. Chem., 2005, 70 (19), pp. 7479-7487.*

* cited by examiner

*Primary Examiner* — Mark Berch
(74) *Attorney, Agent, or Firm* — Oliff & Berridge, PLC

(57) ABSTRACT

A process for the preparation of a carbapenem of formula (I):

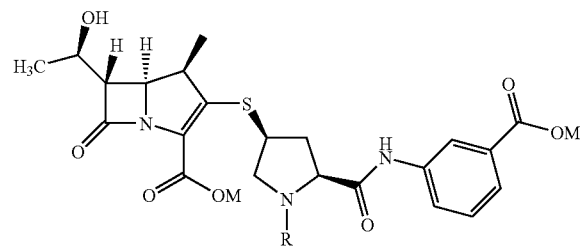

(I)

in amorphous form wherein R represents hydrogen or COOM and M represents hydrogen or sodium the process including condensing a compound of formula (II):

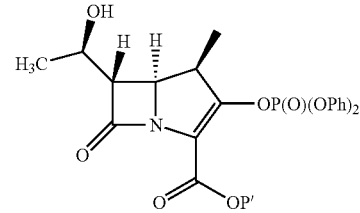

(II)

wherein P' denotes a carboxy protecting group, with a compound of formula (III):

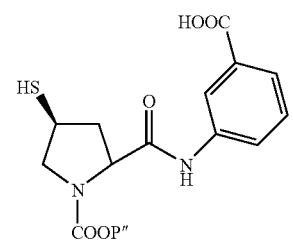

(III)

wherein P" denotes a carboxy protecting group, in the presence of a base to yield a compound of formula (IV):

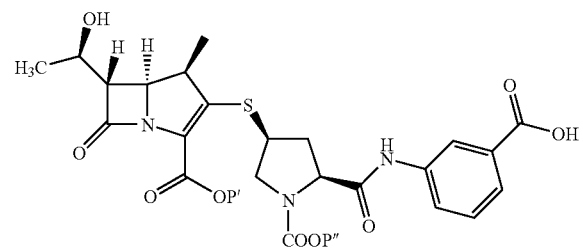

(IV)

deprotecting both the protecting groups in the compound of formula (IV) in the presence or absence of a sodium ion source, a solvent and in the presence or absence of $CO_2$, gas, extracting the product into an aqueous medium, quenching the aqueous layer of into an alcohol at a temperature, and isolating the carbapenem compound of formula (I) in amorphous form.

9 Claims, No Drawings

PROCESS FOR THE PREPARATION OF CARBAPENEM ANTIBIOTIC

FIELD OF THE INVENTION

The present invention relates to an improved process for the preparation of amorphous Ertapenem of formula (I). The present invention further provides novel amorphous form of {sodium salt of 1-Azabicyclo[3.2.0]hept-2-ene-2-carboxylic acid, 3-[[(3S,5S)-5-[[(3-carboxyphenyl)amino]carbonyl]-1-[[(4-nitrophenyl)methoxy]carbonyl]-3-pyrrolidinyl]thio]-6-[(1R)-1-hydroxyethyl]-4-methyl-7-oxo-, 2-[(4-nitrophenyl)methyl]ester, (4R,5S,6S)—} of formula (IV), which is an important intermediate in the preparation of Ertapenem of formula (I).

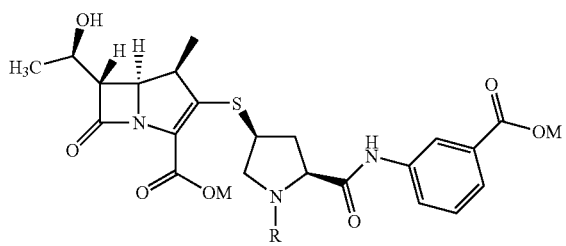

(I)

wherein R represents hydrogen or COOM and M represents hydrogen or sodium ion.

BACKGROUND OF THE INVENTION

Ertapenem sodium is a carbapenem marketed by Merck as Invanz®, and has chemical name [4R,5S,6S]-3-[[(3S,5S)-5-[[(3-carboxyphenyl)amino]carbonyl]-3-pyrrolidinyl]-thio]-6-[(1R)-1-hydroxyethyl]-4-methyl-7-oxo-1-azabicyclo[3.2.0]hept-2-ene-2-carboxylic acid.

Ertapenem of formula (I) is a 1β-methylcarbapenem antibiotic, and used as antibiotic agent in the treatment of moderate to severe complicated foot infection due to indicated pathogens in diabetic patients without osteomyelitis, Ertapenem is also useful in the treatment of pneumonia, urinary tract infections, intra-abdominal, gynecological, skin, and soft tissue infections, meningitis, septicemia and febrile Neutrogena.

In view of the importance of the compound of the formula (I), several synthetic procedures to prepare the compound have been reported.

U.S. Pat. No. 5,478,820 and U.S. Pat. No. 5,856,321 claim various processes for preparing Ertapenem and its sodium salt. Example 12 of U.S. Pat. No. 5,478,820 discloses a process in which the Ertapenem was isolated by using column purification as well as freeze-drying technique. According to Example 4 of this patent disodium salt of Ertapenem was prepared by dissolving crude product in water using NaHCO₃, followed by purification using column chromatography and subsequent lyophilization U.S. Pat. No. 6,504,027 provides a process for preparing Ertapenem in crystalline form which comprises deprotecting and extracting a polar organic solution containing a crude mono-protected Ertapenem of formula

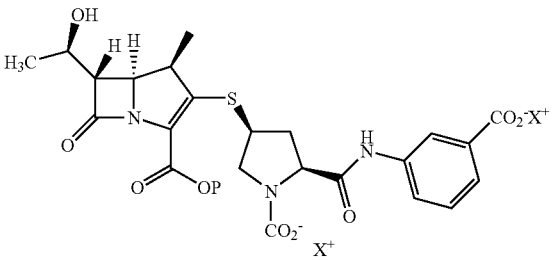

wherein P represents protecting group
with C4-10 alcohol in the presence of ion-pairing reagent followed by adjusting the pH to 5.5, collecting and crystallizing the resultant aqueous phase to produce a crystalline compound. Since this patent involves number of operations like extraction, this process industrially not viable.

U.S. Pat. No. 7,145,002 provides a process for producing Ertapenem or its sodium salt and/or its solvate in crystalline form.

The processes reported in these patents yielded only crystalline compound of Ertapenem or its salt further the said patents utilize a temperature in the range of −5 to −10° C. for crystallization; none of the prior art processes discloses precipitation processes for producing amorphous form of Ertapenem of formula (I). More particularly the above said patents provide only precipitation process for preparing Ertapenem monosodium in crystalline form not its disodium sodium.

With our continued research for developing a process for the preparation of compound of formula (I), we have come up with a process, which is not only commercially viable, but involves simple purification techniques such as crystallization and yields the compound of formula (I) in amorphous form.

OBJECTIVES OF THE INVENTION

The main objective of the present invention is to provide a simple, commercially viable, and industrially scalable process for the preparation of Ertapenem of formula (I) in amorphous form, which avoids techniques like column chromatography, and freeze-drying.

Another objective of the present invention is to provide an amorphous form of Ertapenem of formula (I), which has very good storage stability.

Yet another objective of the present invention is to provide an amorphous form of sodium salt of compound of formula (IV){sodium salt of 1-azabicyclo[3.2.0]hept-2-ene-2-carboxylic acid, 3-[[(3S,5S)-5-[[(3-carboxyphenyl)amino]carbonyl]-1-[[(4-nitrophenyl)methoxy]carbonyl]-3-pyrrolidinyl]thio]-6-[(1R)-1-hydroxyethyl]-4-methyl-7-oxo-, 2-[(4-nitrophenyl)methyl]ester, (4R,5S,6S)—}.

SUMMARY OF THE INVENTION

Accordingly, the present invention provides an improved process for the preparation of Ertapenem of formula (I);

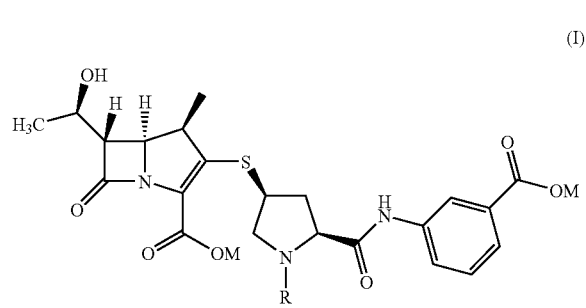

(I)

wherein R represents hydrogen or COOM and M represents hydrogen or sodium ion; the said process comprises the steps of:
  i) condensing the compound of formula (II) with compound of formula (III) in the presence of base and in the presence or absence of solvent to yield the compound of formula (IV) or its sodium salt;
  ii) deprotecting the protecting group in the compound of formula (IV) or its sodium salt in the presence or absence of buffer and in the presence or absence of sodium ion source base and a solvent;
  iii) extracting the product in to aqueous medium; optionally adjusting the pH of the aqueous layer;
  iv) optionally diluting the aqueous layer with a solvent selected from group consisting of acetonitrile or THF; and separating the product-rich oily layer obtained;
  v) quenching the aqueous layer of step (iii) or oily layer of step (iv) to an alcohol selected from group consisting of methanol, isopropyl alcohol, ethanol or mixtures thereof, at a temperature in the range of 0 to 10° C.; and
  vi) isolating the Ertapenem of formula (I) in amorphous form.

The process is shown in Scheme 1:

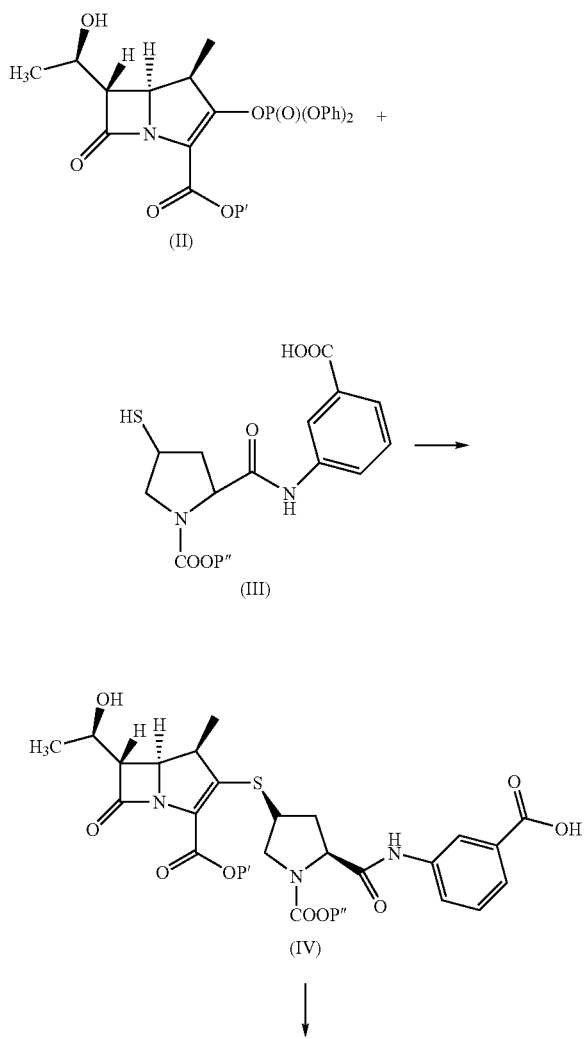

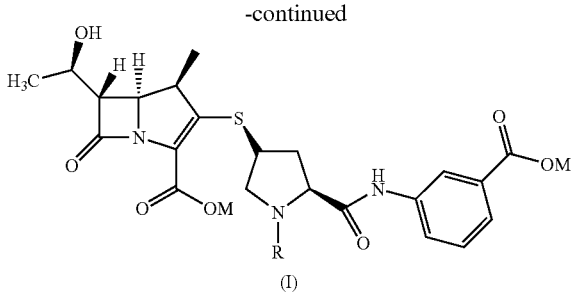

where p and p' represent protecting group.

DESCRIPTION OF THE INVENTION

In an embodiment of the present invention, the protective group represented by P' and P" may be same or different and independently selected from group such as allyl, 2,2,2,-trichloroethyl, 2-bromoethyl, benzhydryl, trityl, aryl, trimethylsilyl, triethylsilyl, 4-methoxybenzyl, t-butyl, p-nitrobenzyl and the like, preferably P and P" is selected from P-nitrobenzyl In another embodiment of the present invention, the solvent used in step (i) is selected from diethyl ether, tetrahydrofuran, toluene, xylene, dichloromethane, 1,2-dichloroethane, N,N-dimethylformamide, dimethylacetamide, N-methylpyrrolidinone, N-ethylpyrrolidinone, N-methylpiperidinone, acetonitrile, propionitrile, and other such organic solvents known in the art or mixtures thereof; and inorganic base used is selected from diisopropylethylamine (DIPEA), diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0.]undec-7-ene (DBU) 1,5-diazabicyclo[4.3.0]non-5-ene (DBN), N-methylpyrrolidine, potassium hydroxide, sodium carbonate, sodium hydrogen carbonate, disodium hydrogen phosphate, and the like preferably diisopropylethylamine. Apart from these bases the condensation reaction may optionally contain bases like N,N-dimethylaminopyridine, N,N-diethylamino pyridine to avoid impurity formation. In another embodiment of the present invention the compound of formula (IV) can be isolated if required as sodium salt, using mixture of ethyl acetate, alcohol and isopropyl ether. The sodium salt was subjected to de-protection to yield Eratapenem sodium. Accordingly the present invention provides novel amorphous form of sodium salt of 1-Azabicyclo[3.2.0]hept-2-ene-2-carboxylic acid, 3-[[(3S,5S)-5-[[(3-carboxyphenyl)amino]carbonyl]-1-[[(4-nitrophenyl)methoxy]carbonyl]-3-pyrrolidinyl]thio]-6-[(1R)-1-hydroxyethyl]-4-methyl-7-oxo-, 2-[(4-nitrophenyl)methyl]ester, (4R,5S,6S)—. The sodium salt of formula (IV) found to be more stable, and easy to handle in industrial point of view.

In another embodiment, the present invention provides a common process for isolation of compound of formula (IV) or its sodium salt which comprises quenching the reaction mass from step (i) into a buffer solution selected from dipotassium hydrogen orthophosphate, or potassium dihydrogen orthophosphate, or water and the like followed by extracting the compound in an organic solvent like ethyl acetate, MDC (dichloromethane) and precipitating the compound of formula (IV) as white to off-white solid in a crystalline or amorphous forms or as a foamy solid directly from the resultant organic layer or by quenching the organic layer into a solvent selected from hexane, heptane, IPE (diisopropylether), methyl tert-butyl ether and the like or mixtures thereof. The intermediate of formula (IV) can be taken to next stage with or without isolation. Alternatively the intermediate of formula (IV) can be directly precipitated from the buffer solution or water.

The reaction conditions for deprotection depend on the nature of the protecting groups utilized. For instance, the 2,2,2-trichloroethoxycarbonyl group is preferably removed by treatment with zinc and glacial acetic acid; Protecting groups such as p-nitrobenzyloxycarbonyl and allyloxycarbonyl are removed by hydrogenolysis, for example by treating with hydrogen in the presence of a noble metal catalyst such as palladium or its complex.

In yet another embodiment of the present invention, the solvent used for deprotection using hydrogenolysis in step (ii) is selected from THF, acetonitrile, dioxane, ethyl acetate, isopropyl alcohol, methanol, dichloromethane, DMF, aqueous carbonic acid (prepared by purging $CO_2$ gas into 4 L water for 2 hrs at about 5° C.), water or mixtures thereof, and catalyst employed for reduction is selected from Palladium on carbon, Platinum, Platinum oxide and the like. The de-protection of protecting groups can be carried out using a mixture of solvents either in single phase or in biphasic medium. The hydrogenation can also optionally be carried out in the presence of buffer like N-morpholinoalkane sulfonic acid like 3-(N-morpholino)propanesulfonic acid (MOPS), 3-(N-morpholino)ethanesulfonic acid (MES). Other buffers that could be used are: 3-(N-morpholino)-2-hydroxypropanesulfonic acid (MOPSO), 3-[N-tris(hydroxymethyl)methylamino]propanesulfonic acid (TAPS), 3-[N-tris(hydroxymethyl)methylamino]-2-hydroxypropanesulfonic acid (TAPSO), N—[N-tris(hydroxymethyl)]-2-aminoethanesulfonic acid (TES), piperazine-N,N'-bis(2-ethanesulfonic acid) (PIPES), 3-(cyclohexylamino)-1-propanesulfonic acid (CAPS), 3-[(3-cholamidopropyl)dimethylammonio]-1-propanesulfonate (CHAPS), N-[2-hydroxyethyl]piperazine-N'-[2-ethanesulfonic acid] (HEPES) and the like. The use of buffer maintains pH of the reaction medium thereby minimizing degradation. If required, the hydrogenation process can employ employs sodium ion source base such as sodium bicarbonate (as disclosed in example 12 of U.S. Pat. No. 5,478,820), sodium hydroxide, and sodium carbonate. The presence of sodium ion source base preferably sodium bicarbonate yielded the compound of formula (I) as disodium salt.

After completion of hydrogenation, the product was taken into aqueous medium, followed by optionally washing with organic solvents like MDC, butyl acetate, ethyl acetate, toluene, hexane, 1,2-dibromoethane and the like to remove reaction by-products and/or impurities. After hydrogenation, optionally carbon dioxide gas was purged to the reaction mass. The aqueous layer was subjected to degassing technique to remove the dissolved solvent if required. Further depending on the requirement, pH of aqueous layer optionally was adjusted using acid like acetic acid, formic acid, HCl, etc to yield the compound of formula (I).

In one more embodiment of the present invention, the aqueous layer containing Eratapenem or its sodium salt was optionally diluted using solvent selected from consisting of acetonitrile, THF, and stirred for a long period, thereby two layers formed. The layer containing the product was separated and quenched into ethanol or IPA to yield the compound, in amorphous form Ertapenem or it sodium salt. Alternatively, the aqueous layer quenched into iso-propyl alcohol (IPA), ethanol, methanol or mixtures thereof to yield amorphous form of Ertapenem of formula (I). Accordingly the present invention provides simple process for the preparation of amorphous form of Ertapenem of formula (I).

In yet another embodiment of the present invention the presence of sodium ion base during hydrogenation yielded compound of formula (I) as disodium salt. The use of sodium bicarbonate (as disclosed in example-12 of U.S. Pat. No. 5,478,820) in hydrogenation yielded the Ertapenem disodium. The aqueous layer containing the Ertapenem disodium was optionally reduced to 5.5 to 7.0 followed by quenching in to an alcohol yielding the compound of formula (I (R=H)) as disodium. Further the isolation of compound of formula (I) without pH adjustment yielded compound of formula (I) as disodium wherein the R represents COOM.

In one more embodiment of the present invention the crystallization process was carried out at a temperature in the range of 0-10° C. The starting material thiol of (III) is prepared by utilizing technique known in the art. For example by following the scheme provided below:

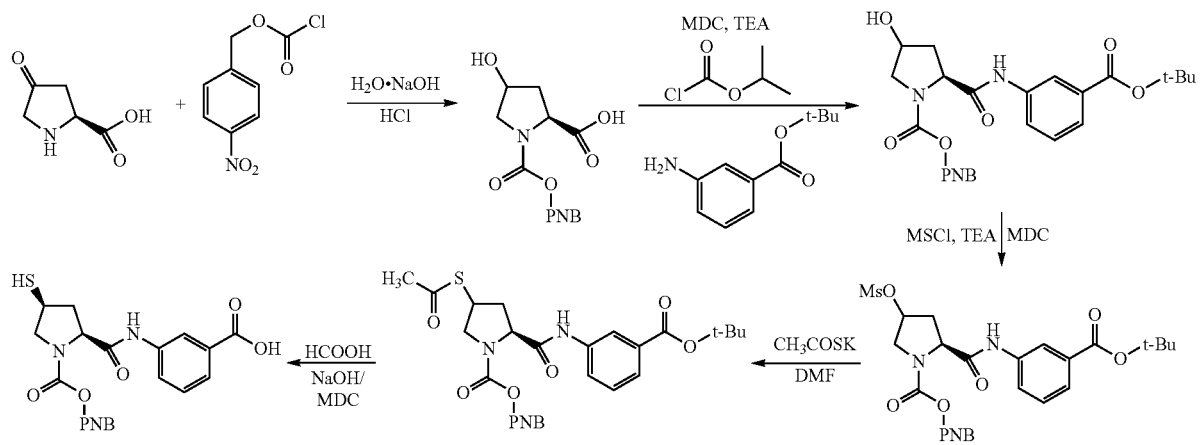

In still another embodiment of the present invention the Ertapenem sodium or disodium obtained was optionally blended with alkali metal carbonate or bicarbonate or with salts like Lysine or Arginine and stored in vial if required under carbon dioxide atmosphere or nitrogen atmosphere. Further the composition may also optionally contain chelating agents like EDTA and buffer like citric acid.

The present invention is illustrated with the following examples, which should not be construed to limit the scope of the invention.

EXAMPLE-1

Preparation of Diprotected Ertapenem of Formula (IV)

To 3-[[[(2S,4S)-4-mercapto-2-pyrrolidinyl-1-(4-nitrobenzyloxy)carbonyl]carbonyl]amino]benzoic acid (8.3 g) in DMF (30 mL), p-nitrobenzyl (1R,5R,6S)-6-[(1R)-1-hydroxyethyl]-2-[(diphenylphosphono)oxy]-1-methylcarbapen-2-em-3-carboxylate (10 g) was added. To the reaction mass, N,N-diisopropylethylamine (5.4 g) was added at −30° C. and stirred. After completion of reaction, the reaction mass was diluted with THF (60 mL) and poured into mixture of buffer solution (pH=7) and ethyl acetate (300 mL). The layers obtained were separated and the filtrate washed with brine solution. The organic layer was subjected to carbon treatment and the filtrate distilled out at 40° C. under vacuum to remove the solvent. The residue was stirred with ethyl acetate (50 mL) to yield title compound of formula (IV) (11 g).

EXAMPLE-2

Preparation of Diprotected Ertapenem of Formula (IV)

To 3-[[[(2S,4S)-4-mercapto-1-(4-nitrobenzyloxy)carbonyl-2-pyrrolidinyl]carbonyl]amino]benzoic acid (7.68 g) in DMF (30 mL), p-nitrobenzyl (1R,5R,6S)-6-[(1R)-1-hydroxyethyl]-2-[(diphenylphosphono)oxy]-1-methylcarbapen-2em-3-carboxylate (10 g) was added. To the reaction mixture N,N-diisopropylethylamine (4.78 g) was added at −30° C. and stirred. After completion of reaction, the reaction mass was poured into water and ethyl acetate mixture at 10° C. The layers were separated and organic layer washed with brine solution. The organic layer was subjected to carbon treatment and taken for subsequent step.

EXAMPLE-3

Preparation of Diprotected Ertapenem of Formula (IV)

To 3-[[[(2S,4S)-4-mercapto-2-pyrrolidinyl-1-(4-nitrobenzyloxy)carbonyl]carbonyl]amino]benzoic acid (8.3 g) in DMF (30 mL), p-nitrobenzyl (1R,5R,6S)-6-[(1R)-1-hydroxyethyl]-2-[(diphenylphosphono)oxy]-1-methylcarbapen-2-em-3-carboxylate (10 g) was added. To the reaction mass N,N-diisopropylethylamine (5.4 g) was added at −30° C. and stirred. After completion of reaction, the reaction mass poured into buffer solution (pH=7) or water. The reaction mass stirred, the solid obtained was filtered and washed with water to yield title compound of formula (IV).

EXAMPLE-4

Preparation of Sodium Salt of Di-Protected Ertapenem (IV)

To a solution of p-nitrobenzyl (1R,5R,6S)-6-[(1R)-1-hydroxyethyl]-2-[(diphenylphosphono)oxy]-1-methylcarbapen-2-em-3-carboxylate of formula (II) (100 g) and 3-[[[(2S,4S)-4-mercapto-1-(4-nitrobenzyloxy)carbonyl-2-pyrrolidinyl]carbonyl]amino]benzoic acid of formula (III) (73.8 g) in DMF, solution of DBU (60 mL) in DMF was added at −50° C., and the reaction mass stirred till completion of reaction. After completion of reaction, the reaction mass quenched into mixture of ethyl acetate and buffer solution (potassium dihydrogen phosphate (175 g) in water or di potassium hydrogen phosphate buffer solution). The pH of biphasic system was adjusted to 4.5 and layers separated. To the organic layer, a solution of sodium-2-ethylhexanoate in ethyl acetate was added (32 g) was added. A pasty mass was obtained. The organic layer was decanted, and the pasty mass dissolved in methanol. The methanol solution was added in IPE to yield the sodium salt of di-protected Ertapenem (IV) (125 g).

EXAMPLE-5

Preparation of Ertapenem Sodium of Formula (I) R=H

To MOPS buffer solution (prepared from 5.5 g MOPS in 100 mL water and pH adjusted to 6-8.5 with sodium hydroxide), diprotected Ertapenem of formula (IV) (10 g) was added and pH adjusted to 7.5 using aqueous sodium hydroxide solution. To this, ethyl acetate (100 mL) was added and stirred to get clear solution at 10-15° C. $CO_2$ gas was purged for 20 mts. To this Pd/C (20 g, 10%) was added and subjected to hydrogenation with 4.5-5.0 Kg pressure at 5-10° C. After completion of reaction, the reaction mass was filtered and the layers separated. The aqueous layer was subjected to carbon treatment and the pH of the filtrate adjusted to 5.5-6.0 followed by stirring with THF (400 mL) for 10 h. The separated oily layer was slowly added into absolute ethanol (100 mL) under stirring at 5° C. The precipitated solid of ertapenem sodium was filtered, washed with ethanol and dried to yield amorphous form of ertapenem sodium. Dry weight: 4.0 g.

EXAMPLE-6

Preparation of Ertapenem Sodium of Formula (I) R=H

To a mixture of MOPS buffer solution (prepared from 13.75 g MOPS in 150 mL water and pH adjusted to 6.0 to 8.5 using NaOH solution), THF (10 mL) and ethyl acetate (200 mL) prepared according to example-2 containing diprotected ertapenem of formula (IV) were added. To this solution, Pd/C (20 g, 10%) was added. This reaction mass was hydrogenated in the presence of hydrogen at 10 to 15 Kg at 5-15° C. After completion of reaction, the mass was filtered and the layers separated. The aqueous layer was washed with ethyl acetate and the pH of aqueous layer, after carbon treatment, was adjusted to pH 5.0 to 6.0 using acetic acid. To the filtrate, acetonitrile (1500 mL) was added and stirred for long period. The oily layer obtained was separated, and slowly added into absolute ethanol (100 mL) under stirring at 5° C. The precipitated solid of ertapenem sodium was filtered, washed with ethanol and dried to yield amorphous form of ertapenem sodium. Dry weight: 4.0 g, water content about 3.0%.

EXAMPLE-7

Preparation of Ertapenem Sodium of Formula (I) R=H

To a solution of sodium salt of di-protected Ertapenem (IV) (20 g) in carbonic acid water, methanol and ethyl acetate (200 mL) in autoclave, Pd/carbon was charged and subjected to hydrogenation with 8 to 10 Kg pressure at 5-10° C. After completion of reaction $CO_2$ gas was purged, the reaction mass filtered and subjected to carbon treatment at a pH in the range of 6.2-6.5. The aqueous layer was separated and washed with mixture of methanol and ethyl acetate. The residual solvents in aqueous layer were removed using degassing technique. The pH of aqueous layer was adjusted to 4.0-5.5 using acetic acid and slowly added into isopropyl alcohol (3.5 L) under stirring at 5° C. The precipitated solid of Ertapenem sodium was filtered, washed with IPA and dried to yield amorphous form of Ertapenem sodium of formula (I).

EXAMPLE-8

Preparation of Ertapenem Sodium of Formula (I) R=H

To a solution of sodium salt of di-protected Ertapenem (IV) (20 g) in carbonic acid water, DMF and ethyl acetate (200 mL) in autoclave, Pd/carbon was charged and subjected to hydrogenation with 8 to 10 Kg pressure at 5-10° C. After completion of reaction, $CO_2$ gas was purged, the reaction mass filtered and subjected to carbon treatment at a pH in the range of 6.2-6.5. The aqueous layer was separated and washed with mixture of methanol, ethyl acetate and MDC. The residual solvents in aqueous layer were removed using degassing technique. The pH of aqueous layer was adjusted to 5.5 using acetic acid and slowly added into absolute isopropyl alcohol (3.5 L) under stirring. The precipitated solid of Ertapenem sodium was filtered, washed with IPA and dried to yield amorphous form of Ertapenem sodium of formula (I).

EXAMPLE-9

Preparation of Ertapenem Disodium of Formula (I) R=H

To the solution of sodium salt of di-protected Ertapenem (IV) (50 g) in carbonic acid water (500 ml), THF (100 ml), DMF (25 ml) and ethyl acetate (1000 mL) and sodium bicarbonate (6.5 gm) in autoclave, Pd/carbon charged and subjected to hydrogenation with 8 to 10 Kg pressure at 5-10° C. After completion of reaction $CO_2$ gas was purged, the reaction mass was filtered. The aqueous layer was separated, washed with ethyl acetate and the residual solvents in aqueous layer removed using degassing technique. The pH of the aqueous layer was adjusted using acetic acid to about 5.5-7.0 and slowly added into mixture of methanol (400 ml) and absolute isopropyl alcohol (6 L) under stirring. The precipitated Ertapenem disodium was filtered, washed with IPA and dried to yield amorphous form of Ertapenem disodium of formula (I). The solid obtained was optionally treated with methanol/isopropyl ether mixture at about −20° C. to yield Ertapenem disodium with low residual solvent content.

EXAMPLE-11

Preparation of Ertapenem Disodium of Formula (I) R=COOM

To the solution of sodium salt of di-protected Ertapenem (IV) (50 g) in carbonic acid water (500 ml), THF (100 ml), DMF (25 ml) and ethyl acetate (1000 mL) and sodium bicarbonate (6.5 gm) in autoclave, Pd/carbon charged and subjected to hydrogenation with 8 to 10 Kg pressure at 5-10° C. After completion of reaction $CO_2$ gas was purged, the reaction mass was filtered. The aqueous layer was separated, washed with ethyl acetate and the residual solvents in aqueous layer removed using degassing technique. The aqueous layer was added in to isopropyl alcohol (12 L) under stirring. The precipitated Ertapenem disodium was filtered, washed with IPA and dried to yield amorphous form of Ertapenem disodium of formula (I). The solid obtained was optionally treated with methanol/isopropyl ether mixture at about −20° C. to yield Ertapenem disodium with low residual solvent content.

We claim:
1. A process for the preparation of carbapenem compound of formula (I):

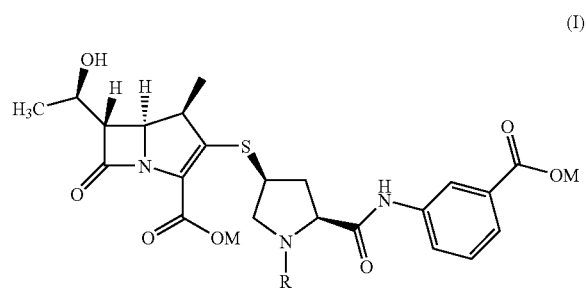

wherein R represents hydrogen and M represents a sodium ion; the process comprising:
i. condensing a compound of formula (II):

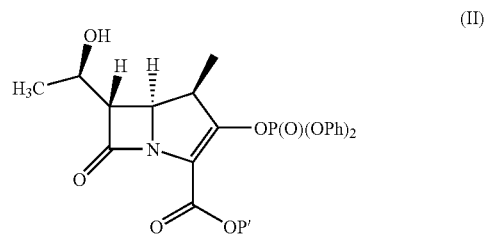

wherein P' denotes a carboxy protecting group,
with a compound of formula (III):

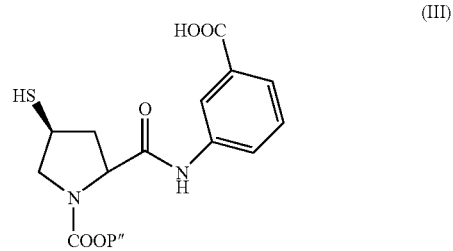

wherein P" denotes a carboxy protecting group,
in the presence of a base to yield a compound of formula (IV) or its sodium salt:

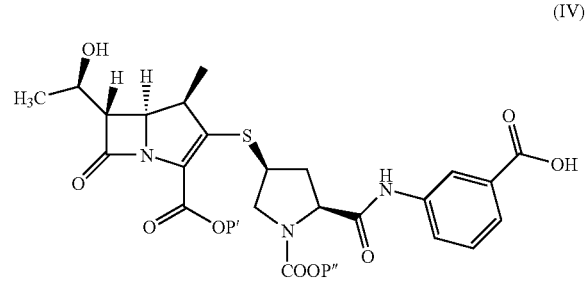

wherein P' and P" have the same meanings as defined above;

ii. deprotecting both of the protecting groups in the compound of formula (IV) or its sodium salt in the presence or absence of sodium ion source, a solvent and in the presence or absence of $CO_2$ gas;
iii. extracting the product into an aqueous medium;
iv. adjusting pH of an aqueous layer in the range of 4.0 to 6.0;
v. quenching the aqueous layer into an alcohol selected from the group consisting of methanol, isopropyl alcohol, ethanol or mixtures thereof, at a temperature in the range of 0 to 10° C.; and
vi. isolating the compound of formula (I) as an amorphous form.

2. The process according to claim 1, wherein the step (i) is performed using a solvent group selected from the group consisting of tetrahydrofuran, toluene, xylene, dichloromethane, 1,2-dichloroethane, N,N-dimethylformamide, N,N-dimethylacetamide, N-methylpyrrolidinone, N-ethylpyrrolidinone, N-methylpiperidinone, acetonitrile, propionitrile, and mixtures thereof.

3. The process according to claim 1 wherein the base used in step (i) is diisopropylethylamine (DIPEA), diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0.] undec-7-ene (DBU), 1,5-diazabicyclo[4.3.0] non-5-ene (DBN), N-methylpyrrolidine, N,N-dimethylaminopyridine, N,N-diethylamino pyridine, potassium hydroxide, sodium carbonate, sodium hydrogen carbonate, or disodium hydrogen phosphate.

4. The process according to claim 1, wherein the solvent used in step (ii) is THF, acetonitrile, dioxane, ethyl acetate, isopropyl alcohol, methanol, dichloromethane, DMF, aqueous carbonic acid, buffer solution, water or mixtures thereof.

5. The process according to claim 1, wherein the sodium ion source used in step (ii) is selected from the group consisting of sodium carbonate, sodium hydroxide, sodium bicarbonate and mixtures thereof.

6. The process according to claim 1, wherein the protecting group represented by P''' or P' is allyl, 2,2,2,-trichloroethyl, 2-bromoethyl, benzhydryl, trityl, arylmethyl, trimethysilyl, triethylsilyl, 4-methoxybenzyl, t-butyl, or p-nitrobenzyl.

7. The process according to claim 1, wherein the deprotection of the compound of formula (IV) or its sodium salt is done by treating the compound with hydrogen gas in the presence of a noble metal catalyst.

8. The process according to claim 7, wherein the noble metal catalyst is palladium on carbon, platinum or platinum oxide.

9. An amorphous form of a sodium salt of 1-Azabicyclo [3.2.0]hept-2-ene-2-carboxylic acid, 3-[[(3S,5S)-5-[[(3-carboxyphenyl)amino]carbonyl]-1-[[(4-nitrophenyl)methoxy] carbonyl]-3-pyrrolidinyl]thio]-6-[(1R)-1-hydroxyethyl]-4-methyl-7-oxo-, 2-[(4-nitrophenyl)methyl]ester, (4R,5S,6S)- of formula (IV):

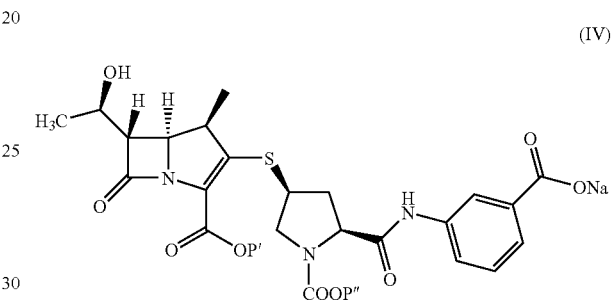

(IV)

wherein P' and P''' represents p-nitrobenzyl.

* * * * *